Figure 1:
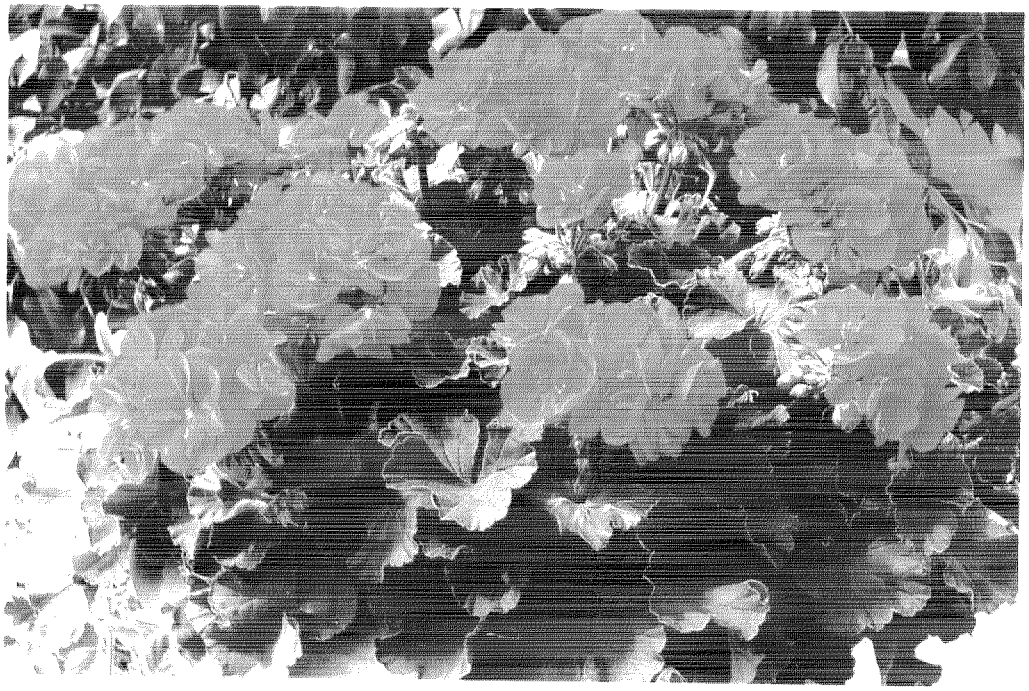

US00PP10961P

United States Patent [19]

Hanes

[11] Patent Number: Plant 10,961

[45] Date of Patent: Jun. 15, 1999

[54] GERANIUM PLANT NAMED 'CLIPS CHERRY'

[75] Inventor: Mitchell Eugene Hanes, Morgan Hill, Calif.

[73] Assignee: Goldsmith Seeds, Inc., Gilroy, Calif.

[21] Appl. No.: 08/968,763

[22] Filed: Nov. 6, 1997

[51] Int. Cl.[6] ..... A01H 5/00

[52] U.S. Cl. ..... Plt./329

[58] Field of Search ..... Plt./87.12, 325, Plt./328, 329, 330

[56] References Cited

PUBLICATIONS

UPOV-ROM, 1998/01, Plant Variety Database, GTI Jouve Retrieval Software, citation for 'Clips Cherry'.

*Primary Examiner*—Howard J. Locker

*Attorney, Agent, or Firm*—Rothwell, Figg, Ernst & Kurz

[57] ABSTRACT

A new geranium cultivar particularly distinguished by dark green foliage with light zonation, carmine flower color, and semi-double flowers on large umbels.

1 Drawing Sheet

BACKGROUND OF THE NEW PLANT

The present invention comprises a new and distinct cultivar of geranium, botanically known as *Pelargonium hortorum* Bailey, and hereinafter referred to by the cultivar name Clips Cherry. The new cultivar is propagated from a seedling resulting from the cross of a seed parent 4158-2, a red colored, single flower form with dark foliage and the pollen parent Americana Violet (U.S. Plant Pat. No. 8,750), a violet colored, semi-double flower with green foliage.

Clips Cherry is a product of a planned breeding program intended to create new geranium cultivars with carmine colored flowers, semi-double flower form, green foliage, vigorous growth and superior cutting productivity.

The new cultivar was created in 1994 in Gilroy, Calif. and has been repeatedly asexually reproduced by cuttings in Gilroy, Calif. and Guatemala over a three year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit including the bloom.

DESCRIPTION OF THE NEW CULTIVAR

The following detailed descriptions set forth the distinctive characteristics of Clips Cherry. The data which defines these characteristics were collected from asexual reproductions carried out by Goldsmith Seeds, Inc. in Gilroy, Calif. The plant history was taken on 18 week old plants, blossomed under natural light in a greenhouse and color readings were taken in the greenhouse in Gilroy, Calif. on May 19, 1997 in the afternoon under ambient light. Color references are primarily to The R.H.S. Colour Chart of The Royal Horticultural Society of London (R.H.S.).

THE PLANT

Classification:

*Botanical.*—*Pelargonium hortorum* Bailey.

*Commercial.*—Zonal geranium.

Form: Upright with moderate branching.

Height: 16 cm, as a 4½ inch pot plant, excluding blooms.

Foliage: Abundant quantity.

Finishing time: Finishing time of a 4-inch pot from a rooted cutting is 12 weeks.

Leaves:

*Size.*—Diameter about 7.5 cm.

*Shape.*—Rounded cordate with occasional up folding between veins.

*Margin.*—Irregularly crenate.

*Texture.*—Leathery and pubescent on both surfaces, especially along veins.

*Ribs and veins.*—Distinctly palmate, 2.3 to 4.0 cm long.

*Color.*—Upper side: Dark green 137A R.H.S. with light zonation 147A R.H.S. Under side: Lighter green 137C R.H.S. color. Ribs and veins not prominently different from upper surface.

*Petioles.*—About 6 to 6.5 cm in length, green 137C R.H.S.

THE BUD

Size:

*Diameter.*—About 9 mm.

*Length.*—About 2.5 cm at time of bud opening.

Shape: Pointed ovoid.

Color: Petals when sepals first divide, 57A R.H.S.

Sepals: 5 in number, flat behind petals. Pointed linear lanceolate, R.H.S. 143A in an open flower.

THE FLOWER

Blooming habit: Continuous throughout the year.

Size: Approximatley 4.6 cm in diameter, 1.5 cm deep, irregularly radially symmetrical.

Form: Cup-shaped when bloom first opens, later flattening to shallow cup shape with maturity.

Petals: 6 imbricate outer petals, 2.3–2.6 cm wide and approximately 3.0 cm long. Five to seven inner smaller petaloids of varying shape. Both the outer petals and inner petaloids are carmine 57A R.H.S. Veins slightly darker than interveinal regions. Underside of petals lighter. Petals and petaloids soft and satiny.

Pedicel: Approximately 2.3 cm in length, green 146B R.H.S.

Persistence: Non-shattering flower.

INFLORESCENCE

Type: An umbel composed of approximately 35 flowers, erect or laterally ascending that has a diameter of approximately 10 cm and is held about 4 cm over foliage.

Peduncle: Approximately 11 cm in length. Green 146C R.H.S. with purple tint.

REPRODUCTIVE ORGANS

Stamens:

*Anthers.*—Approximately 6 anthers positioned below the mature stigma, dull red prior to anthesis.

*Filaments.*—White near base and mid length, graduating to dull red near anther.

*Pollen.*—Orange in color.

Pistil:

*Number.*—1.

*Length.*—Approximately 7 mm.

*Stigma.*—5 linear lobes of near equal length, curling back toward ovary, purplish-red in color.

*Style.*—Length: About 3 mm Color: Purplish red.

*Ovaries.*—At anthesis, densely pubescent with white hairs, oblong. Green drying to a light brown at maturity.

*Fruit.*—Will set some seed.

I claim:

1. A new and distinct cultivar of geranium plant substantially as herein shown and described, named Clips Cherry, that is characterized by: dark green foliage with light zonation, carmine flower color, and semi-double flowers on large umbels.

* * * * *